(12) United States Patent
Farese, Jr. et al.

(10) Patent No.: US 6,344,548 B1
(45) Date of Patent: Feb. 5, 2002

(54) DIACYLGLYCEROL O-ACYLTRANSFERASE

(75) Inventors: Robert V. Farese, Jr.; Sylvaine Cases; Steven Smith; Sandra K. Erickson, all of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/103,754

(22) Filed: Jun. 24, 1998

(51) Int. Cl.[7] .............................................. C07H 21/04
(52) U.S. Cl. ...................................... 536/23.2
(58) Field of Search ...................... 536/23.2; 435/69.1, 435/440, 455, 468, 471

(56) References Cited

FOREIGN PATENT DOCUMENTS

WO          97/45439          12/1997

OTHER PUBLICATIONS

Katavic, V., et al., "Alteration Of Seed Fatty Acid Composition By An Ethyl Methanesulfonate–Induced Mutation In *Arabidopsis thaliana* Affecting Diacylglycerol Acyltransferase Activity," Plant Physiology 91995) vol., 108:399–409.

Andersson, Maria, et al., "Purification Of Diacylglycerol:Acyltransferase From Rat Liver To Near Homogeneity," *Journal of Lipid Research* (1994) vol. 35:535–545.

Cases, Sylvaine, et al., "Cloning And Expression Of A Candidate Gene For Diacyglycerol Acyltransferase," *The FASEB Journal* (Mar. 20, 1998) vol. 12, No. (5):A814.

Kamisaka, Yasushi, et al., "Purification and Characterization Of Diacylglycerol Acyltransferase From The Lipid Body Fraction Of An Oleaginous Fungus," *J. Biochem.* (1997) vol. 121, No. (6):1107–1114.

Lehner, Richard et al., "Triacylglycerol Synthesis By Purified Triacylglycerol Synthetase Of Rat Intestinal Mucosa," *The Journal of Biological Chemistry* (Jun. 9, 1995) vol. 270, No. (23):13630–13636.

Little, Dawn, et al., "Solubilization And Characterization Of Diacylglycerol Acyltransferase From Microspore–Derived Cultures Of Oilseed Rape," *Biochem. J.* (1994) vol. 304:951–958.

Newman, T., et al., "Genes Galore: A Summary Of Methods For Accessing Results From Large–Scale Partial Sequencing Of Anonymous Arabidopsis cDNA Clones," *Plant Physiol.* (Dec. 1994) vol. 106, No. (4):1241–1255.

Zou, Jitao, et al., "Cloning Of A cDNA Encoding The 21.2 kDa Oleosin Isoform From *Arabidopsis Thaliana* And A Study Of Its Expression In A Mutant Defective In Diacylglycerol Acyltransferase Activity[1]," *Plant Molecular Biology* (1996) vol. 31:429–433.

van de Loo et al. PNAS, USA 92:6743–6747, Jul. 1995.*

* cited by examiner

Primary Examiner—Elizabeth F. McElwain
(74) Attorney, Agent, or Firm—Bret E. Field; Bozicevic, Field & Francis

(57) ABSTRACT

Nucleic acid compositions encoding polypeptide products with diglyceride acyltransferase activity, as well as the polypeptide products encoded thereby and methods for producing the same, are provided. The subject polypeptide and nucleic acid compositions find use in a variety of applications, including research, diagnostic, and therapeutic agent screening applications, as well as in treatment therapies and in the production of triacylglycerols.

4 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 261 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CAGAGGCCTG AGCTGCACCT GAGGGGCTGG CTTCTCACTG CCACCTCACA CCCGCTGGCA      60

GAGCCCACCT CTCCTCCTAG GCCTCGAGTT GCTGGGGATG GGCCTGGCTG CACAGCATCC     120

TCCTCTGGTC CCAGGGAGGC CTCTCTGCCC CTATGGGGCT CTGTCCTGCA CCCCTCAGGG     180

ATGGCGACAG CAGGCCAGAC ACAGTCTGAT GCCAGCTGGG AGTCTTGCTG ACCCTGCCCC     240

GGGTCCGAGG GTGTCAATAA A                                               261
```

(2) INFORMATION FOR SEQ ID NO:2:

(i) SEQUENCE CHARACTERISTICS:
       (A) LENGTH: 1650 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

```
GGATGAATGG AAATAAGTAG AATTAGGCAT ACTTAGGATA GGGCTCAAGC CGCGGCCCGT      60

GAAGATTGGG CCGCGACGAG GTGCGGGCCG AAGCCATGGG CGACCGCGGA GGCGCGGGAA     120

GCTCTCGGCG TCGGAGGACC GGCTCGCGGG TTTCCGTCCA GGGTGGTAGT GGGCCCAAGG     180

TAGAAGAGGA CGAGGTGCGA GACGCGGCTG TGAGCCCCGA CTTGGGCGCC GGGGGTGACG     240

CGCCGGCTCC GGCTCCGGCT CCAGCCCATA CCCGGGACAA AGACGGGCGG ACCAGCGTGG     300

GCGACGGCTA CTGGGATCTG AGGTGCCATC GTCTGCAAGA TTCTTTGTTC AGCTCAGACA     360

GTGGTTTCAG CAATTATCGT GGTATCCTGA ATTGGTGTGT GGTGATGCTG ATCCTGAGTA     420

ATGCAAGGTT ATTTTTAGAG AACCTTATCA AGTATGGCAT CCTGGTGGAT CCTATCCAGG     480

TGGTGTCTCT GTTTTTGAAG GACCCCTACA GCTGGCCTGC CCCATGCGTG ATTATTGCAT     540

CCAATATTTT TGTTGTGGCT GCATTTCAGA TTGAGAAGCG CCTGGCAGTG GGTGCCCTGA     600

CAGAGCAGAT GGGGCTGCTG CTACATGTGG TTAACCTGGC CACAATCATT TGCTTCCCAG     660

CAGCTGTGGC CTTACTGGTT GAGTCTATCA CTCCAGTGGG TTCCGTGTTT GCTCTGGCAT     720

CATACTCCAT CATGTTCCTC AAGCTTTATT CCTACCGGGA TGTCAACCTG TGGTGCCGCC     780

AGCGAAGGGT CAAGGCCAAA GCTGTCTCTA CAGGGAAGAA GGTCAGTGGG GCTGCTGCCC     840

AGCAAGCTGT GAGCTATCCA GACAACCTGA CCTACCGAGA TCTCTATTAC TTCATCTTTG     900

CTCCTACTTT GTGTTATGAA CTCAACTTTC CTCGGTCCCC CGCAATACGA AAGCGCTTTC     960

TGCTACGACG AGTTCTTGAG ATGCTCTTTT TTACCCAGCT TCAAGTGGGG CTGATCCAAC    1020

AGTGGATGGT CCCTACTATC CACAACTCCA TGAAGCCCTT CAAGGATATG GACTATTCAC    1080
```

```
GGATCATTGA GCGTCTCTTA AAGCTGGCGG TCCCCAACCA TCTGATCTGG CTTATCTTCT    1140

TCTATTGGTT TTTCCACTCC TGTCTCAATG CTGTGGCAGA GCTTCTGCAG TTTGGAGACC    1200

GCGAGTTCTA CAGAGATTGG TGGAATGCTG AGTCTGTCAC CTACTTTTGG CAGAACTGGA    1260

ATATCCCCGT GCACAAGTGG TGCATCAGAC ACTTCTACAA GCCTATGCTC AGACATGGCA    1320

GCAGCAAATG GGTGGCCAGG ACAGGAGTAT TTTTGACCTC AGCCTTCTTC CATGAGTACC    1380

TAGTGAGCGT TCCCCTGCGG ATGTTCCGCC TCTGGGCATT CACAGCCATG ATGGCTCAGG    1440

TCCCACTGGC CTGGATTGTG GGCCGATTCT TCCAAGGGAA CTATGGCAAT GCAGCTGTGT    1500

GGGTGACACT CATCATTGGG CAACCGGTGG CTGTGCTCAT GTATGTCCAC GACTACTACG    1560

TGCTCAACTA CGATGCCCCA GTGGGGGTAT GAGCTACTGC CAAAGGCCAG CCCTCCCTAA    1620

CCTGGGCCTG GAGTTCTGGA GGGGTTCCTG                                    1650

(2) INFORMATION FOR SEQ ID NO:3:

(i) SEQUENCE CHARACTERISTICS:
         (A) LENGTH: 629 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

TGCATGTATA CGGAAGGGTT GGGTGGCTCG TCAATTTGCA AAACTGGTCA TATTCACCGG      60

ATTCATGGGA TTTATAATAG AACAATATAT AAATCCTATT GTCAGGAACT CAAAGCATCC     120

TTTGAAAGGC GATCTTCTAT ATGCTATTGA AAGAGTGTTG AAGCTTTCAG TTCCAAATTT     180

ATATGTGTGG CTCTGCATGT TCTACTGCTT CTTCCACCTT TGGTTAAACA TATTGGCAGA     240

GCTTCTCTGC TTCGGGGATC GTGAATTCTA CAAAGATTGG TGGAATGCAA AAAGTGTGGG     300

AGATTACTGG GAGAATGTGG AATATGCCTG TCCATAAATG GGATGGGTCC GACATATATA     360

CCTTCCCCGT GCTTGCGCAC AAGGATTACC CAAAGACACC CCGGCCATTA ACCATTGGCT     420

TTCCCAAGCC CCCTGGAGGC CTTTCCATGG GCCANGGACC CGGNGTNCCC TGGCNGGCCC     480

TTCAAAGCAA AGGGGGNTTN CCTGGGGNTA AAGNTCCANG GGCCCTTGGG GCCCANCCAA     540

AANNTTCCCC CGGGAAAGGG TTGCCCACCG GGGGGNGAAA AANNCCCGGG GGCACCNCGG     600

AATTTTGGGA ACCCGGGGGG GGCCTTTTT                                      629

(2) INFORMATION FOR SEQ ID NO:4:

(i) SEQUENCE CHARACTERISTICS:
         (A) LENGTH: 386 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Leu Phe Leu Glu Asn Leu Ile Lys Tyr Gly Ile Leu Val Asp Pro Ile
  1               5                  10                  15

Gln Val Val Ser Leu Phe Leu Lys Asp Pro Tyr Ser Trp Pro Ala Pro
                 20                  25                  30

Cys Leu Val Ile Ala Ala Asn Val Phe Ala Val Ala Ala Phe Gln Val
             35                  40                  45

Glu Lys Arg Leu Ala Val Gly Ala Leu Thr Glu Gln Ala Gly Leu Leu
         50                  55                  60
```

```
Leu His Val Ala Asn Leu Ala Thr Ile Leu Cys Phe Pro Ala Ala Val
65                  70                  75                  80

Val Leu Leu Val Glu Ser Ile Thr Pro Val Gly Ser Leu Leu Ala Leu
                85                  90                  95

Met Ala His Thr Ile Leu Phe Leu Lys Leu Phe Ser Tyr Arg Asp Val
            100                 105                 110

Asn Ser Trp Cys Arg Arg Ala Arg Ala Lys Ala Ala Ser Ala Gly Lys
        115                 120                 125

Lys Ala Ser Ser Val Ala Ala Pro His Thr Val Ser Tyr Pro Asp Asn
130                 135                 140

Leu Thr Tyr Arg Asp Leu Tyr Tyr Phe Leu Phe Ala Pro Thr Leu Cys
145                 150                 155                 160

Tyr Glu Leu Asn Phe Pro Arg Ser Pro Arg Ile Arg Lys Arg Phe Leu
                165                 170                 175

Leu Arg Arg Ile Leu Glu Met Leu Phe Phe Thr Gln Leu Gln Val Gly
            180                 185                 190

Leu Ile Gln Gln Trp Met Val Pro Thr Ile Gln Asn Ser Met Lys Pro
        195                 200                 205

Phe Lys Asp Met Asp Tyr Ser Arg Ile Ile Glu Arg Leu Leu Lys Leu
    210                 215                 220

Ala Val Pro Asn His Leu Ile Trp Leu Ile Phe Phe Tyr Trp Leu Phe
225                 230                 235                 240

His Ser Cys Leu Asn Ala Val Ala Glu Leu Met Gln Phe Gly Asp Arg
                245                 250                 255

Glu Phe Tyr Arg Asp Trp Trp Asn Ser Glu Ser Val Thr Tyr Phe Trp
            260                 265                 270

Gln Asn Trp Asn Ile Pro Val His Lys Trp Cys Ile Arg His Phe Tyr
        275                 280                 285

Lys Pro Met Leu Arg Arg Gly Ser Ser Lys Trp Met Ala Arg Thr Gly
    290                 295                 300

Val Phe Leu Ala Ser Ala Phe Phe His Glu Tyr Leu Val Ser Val Pro
305                 310                 315                 320

Leu Arg Met Phe Arg Leu Trp Ala Phe Thr Gly Met Met Ala Gln Ile
                325                 330                 335

Pro Leu Ala Trp Phe Val Gly Arg Phe Phe Gln Gly Asn Tyr Gly Asn
            340                 345                 350

Ala Ala Val Trp Leu Ser Leu Ile Ile Gly Gln Pro Ile Ala Val Leu
        355                 360                 365

Met Tyr Val His Asp Tyr Tyr Val Leu Asn Tyr Glu Ala Pro Ala Ala
    370                 375                 380

Glu Ala
385

(2) INFORMATION FOR SEQ ID NO:5:

(i) SEQUENCE CHARACTERISTICS:
        (A) LENGTH: 498 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Gly Asp Arg Gly Gly Ala Gly Ser Ser Arg Arg Arg Arg Thr Gly
1               5                   10                  15
```

-continued

```
Ser Arg Val Ser Val Gln Gly Gly Ser Gly Pro Lys Val Glu Glu Asp
            20                  25                  30

Glu Val Arg Asp Ala Ala Val Ser Pro Asp Leu Gly Ala Gly Gly Asp
            35                  40                  45

Ala Pro Ala Pro Ala Pro Ala Pro Ala His Thr Arg Asp Lys Asp Gly
 50                  55                  60

Arg Thr Ser Val Gly Asp Gly Tyr Trp Asp Leu Arg Cys His Arg Leu
 65                  70                  75                  80

Gln Asp Ser Leu Phe Ser Ser Asp Ser Gly Phe Ser Asn Tyr Arg Gly
                85                  90                  95

Ile Leu Asn Trp Cys Val Val Met Leu Ile Leu Ser Asn Ala Arg Leu
                100                 105                 110

Phe Leu Glu Asn Leu Ile Lys Tyr Gly Ile Leu Val Asp Pro Ile Gln
                115                 120                 125

Val Val Ser Leu Phe Leu Lys Asp Pro Tyr Ser Trp Pro Ala Pro Cys
            130                 135                 140

Val Ile Ile Ala Ser Asn Ile Phe Val Val Ala Ala Phe Gln Ile Glu
145                 150                 155                 160

Lys Arg Leu Ala Val Gly Ala Leu Thr Glu Gln Met Gly Leu Leu Leu
                165                 170                 175

His Val Val Asn Leu Ala Thr Ile Ile Cys Phe Pro Ala Ala Val Ala
                180                 185                 190

Leu Leu Val Glu Ser Ile Thr Pro Val Gly Ser Val Phe Ala Leu Ala
                195                 200                 205

Ser Tyr Ser Ile Met Phe Leu Lys Leu Tyr Ser Tyr Arg Asp Val Asn
210                 215                 220

Leu Trp Cys Arg Gln Arg Val Lys Ala Lys Ala Val Ser Thr Gly
225                 230                 235                 240

Lys Lys Val Ser Gly Ala Ala Gln Gln Ala Val Ser Tyr Pro Asp
                245                 250                 255

Asn Leu Thr Tyr Arg Asp Leu Tyr Tyr Phe Ile Phe Ala Pro Thr Leu
                260                 265                 270

Cys Tyr Glu Leu Asn Phe Pro Arg Ser Pro Arg Ile Arg Lys Arg Phe
                275                 280                 285

Leu Leu Arg Arg Val Leu Glu Met Leu Phe Phe Thr Gln Leu Gln Val
            290                 295                 300

Gly Leu Ile Gln Gln Trp Met Val Pro Thr Ile His Asn Ser Met Lys
305                 310                 315                 320

Pro Phe Lys Asp Met Asp Tyr Ser Arg Ile Ile Glu Arg Leu Leu Lys
                325                 330                 335

Leu Ala Val Pro Asn His Leu Ile Trp Leu Ile Phe Phe Tyr Trp Phe
                340                 345                 350

Phe His Ser Cys Leu Asn Ala Val Ala Glu Leu Leu Gln Phe Gly Asp
                355                 360                 365

Arg Glu Phe Tyr Arg Asp Trp Trp Asn Ala Glu Ser Val Thr Tyr Phe
            370                 375                 380

Trp Gln Asn Trp Asn Ile Pro Val His Lys Trp Cys Ile Arg His Phe
385                 390                 395                 400

Tyr Lys Pro Met Leu Arg His Gly Ser Ser Lys Trp Val Ala Arg Thr
                405                 410                 415

Gly Val Phe Leu Thr Ser Ala Phe Phe His Glu Tyr Leu Val Ser Val
                420                 425                 430
```

```
Pro Leu Arg Met Phe Arg Leu Trp Ala Phe Thr Ala Met Met Ala Gln
        435                 440                 445

Val Pro Leu Ala Trp Ile Val Gly Arg Phe Phe Gln Gly Asn Tyr Gly
        450                 455                 460

Asn Ala Ala Val Trp Val Thr Leu Ile Ile Gly Gln Pro Val Ala Val
465                 470                 475                 480

Leu Met Tyr Val His Asp Tyr Tyr Val Leu Asn Tyr Asp Ala Pro Val
                485                 490                 495

Gly Val (2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Met Gly Asp Tyr Lys Asp Asp Asp Asp Gly
1               5                   10
```

DIACYLGLYCEROL O-ACYLTRANSFERASE

ACKNOWLEDGMENT OF GOVERNMENT SUPPORT

This invention was made with Government support under Grant Nos. R01 52069 and R01 57170 awarded by the National Institute of Health and support from the Veteran's Administration. The Government has certain rights in this invention.

INTRODUCTION

1. Field of the Invention

The field of the invention is enzymes, particularly acyltransferases.

2. Background of the Invention

Diacylglycerol O-Acyltransferase (EC 2.3.1.20), also known as diglyceride acyltransferase or DGAT, is a critical enzyme in triacylglycerol synthesis. Triacylglycerols are quantitatively the most important storage form of energy for eukaryotic cells. DGAT catalyzes the rate-limiting and terminal step in triacylglycerol synthesis using diacylglycerol and fatty acyl CoA as substrates. As such, DGAT plays a fundamental role in the metabolism of cellular diacylglycerol and is important in higher eukaryotes for intestinal fat absorption, lipoprotein assembly, fat storage in adipocytes, milk production and possibly egg production and sperm maturation.

Because of its central role in a variety of different processes, including those rocesses listed above, there is intense interest in the characterization of DGAT. To this end, several groups have undertaken the purification of DGAT from a variety of different sources. However, the inventors are not aware of any report in which a polynucleotide encoding DGAT has been identified or cloned.

As such, there is much interest in the identification of polynucleotides encoding proteins having DGAT activity, as well as the proteins encoded thereby.

RELEVANT LITERATURE

References describing at least partial purification of DGAT from naturally occurring sources include: Kamisaka et al., "Purification and Characterization of Diacylglycerol Acyltransferase from the Lipid Body Fraction of Oleaginous Fungus," J. Biochem (Tokyo) 1997 (6) 1107–1114; Little et al., "Solubilization and Characterization of Diacylglycerol Acyltransferase from Microspore-Derived Cultures of Oilseed Rape," Biochem J. (Dec. 15, 1994) 304 (Pt 3): 951–958; Andersson et al., "Purification of Diacylglycero-l:acyltransferase from Rat Liver to Near Homogeneity," J. Lipid Res. (March 1994) 35: 535–545; Polokoff & Bell, "Solubilization, Partial Purification and Characterization of Rat Liver Microsomal Diacylglycerol Acyltransferase," Biochim. Biophys. Acta (1980) 618: 129–142.

References describing the role DGAT plays in various biological processes include: Bell & Coleman, "Enzymes of Glycerolipid Synthesis in Eukaryotes," Annu. Rev. Biochem. (1980) 49: 459–487; Lehner & Kuksis, "Biosynthesis of Triacylglycerols," Prog. Lipid Res. (1996) 35: 169–201; Brindley, Biochemistry of Lipids, Lipoproteins and Membranes (eds. Vance & Vance)(Elsevier, Amsterdam)(1991) pp171–203; Haagsman & Van Golde, "Synthesis and Secretion of Very Low Density Lipoproteins by Isolated Rat Hepatocytes in Suspension: Role of Diacylglycerol Acyltransferase," Arch. Biochem. Biophys. (1981) 208:395–402; Coleman & Bell, "Triacylglycerol Synthesis in Isolated Fat Cells. Studies on the Microsomal Diacylglycerol Acyltransferase Activity Using Ethanol-Dispersed Diacylglycerols," J. Biol. Chem. (1976) 251:4537–4543.

SUMMARY OF THE INVENTION

Nucleic acid compositions encoding polypeptide products with diglyceride acyltransferase activity, as well as the polypeptide products encoded thereby and methods for producing the same, are provided. Also provided are: methods and compositions for modulating DGAT activity; DGAT transgenic cells, animals and plants, as well as methods for their preparation; and methods for making triglycerides and triglyceride compositions, as well as the compositions produced by these methods. The subject methods and compositions find use in a variety of different applications, including research, medicine, agriculture and industry.

DETAILED DESCRIPTION OF THE INVENTION

Nucleic acid compositions encoding polypeptide products with diglyceride acyltransferase activity, as well as the polypeptide products encoded thereby and methods for producing the same, are provided. Also provided are: methods and compositions for modulating DGAT activity, e.g. in the treatment of disease conditions associated with DGAT activity; DGAT transgenic cells, animals, plants and fungi, and methods for their preparation, e.g. for use in research, food production, industrial feedstock production, etc.; and methods for making triglycerides and triglyceride compositions, e.g. oils. The methods and compositions of the subject invention find use in a variety of different applications and fields, including research, medicine, agriculture and industry.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

NUCLEIC ACID COMPOSITIONS

Nucleic acid compositions encoding polypeptide products, as well as fragments thereof, having diglyceride acetyltransferase (DGAT) activity are provided. By nucleic acid composition is meant a composition comprising a sequence of DNA having an open reading frame that encodes a DGAT polypeptide, i.e. a gene encoding a polypeptide having DGAT activity, and is capable, under appropriate conditions, of being expressed as a DGAT polypeptide. Also encompassed in this term are nucleic acids that are homologous or substantially similar or identical to the nucleic acids encoding DGAT polypeptides or proteins. Thus, the subject invention provides genes encoding mammalian DGAT, such as genes encoding human DGAT and homologs thereof and mouse DGAT and homologs thereof, as well as plant DGAT, such as Arabidopsis thaliana DGAT and homologs thereof. In other words, both animal and plant genes encoding DGAT proteins are provided by the subject invention. The coding sequence of the human DGAT gene, i.e. the human cDNA encoding the human DGAT enzyme, comprises the nucleic acid sequence substantially the same as or identical to that identified as SEQ ID NO:01, infra. The coding sequence of the mouse DGAT gene, i.e. the mouse cDNA encoding the mouse DGAT enzyme, has the nucleic acid sequence identified as SEQ ID NO:02, infra. The coding sequence of the A. thaliana DGAT gene, i.e. the A.thaliana cDNA encoding the A. thaliana DGAT enzyme, comprises the nucleic acid sequence identified as SEQ ID NO:03, infra.

The source of homologous genes to those specifically listed above may be any species, including both animal and plant species, e.g., primate species, particularly human; rodents, such as rats and mice, canines, felines, bovines, ovines, equines, yeast, nematodes, etc. Between mammalian species, e.g., human and mouse, homologs have substantial sequence similarity e.g at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings). The sequences provided herein are essential for recognizing DGAT-related and homologous polynucleotides in database searches.

Nucleic acids encoding the DGAT proteins and DGAT polypeptides of the subject invention may be cDNAs or genomic DNAs, as well as fragments thereof The term "DGAT-gene" shall be intended to mean the open reading frame encoding specific DGAT proteins and polypeptides, and DGAT introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a DGAT protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject DGAT proteins and polypeptides, described in greater detail infra. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The DGAT-genes of the subject invention are isolated and obtained in substantial purity, generally as other than an intact chromosome. Usually, the DNA will be obtained substantially free of other nucleic acid sequences that do not include a DGAT sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of the DGAT polypeptides, as described below.

POLYPEPTIDE COMPOSITIONS

Also provided by the subject invention are polypeptides having DGAT activity, i.e. capable of catalyzing the acylation of diacylglycerol. In addition to being capable of catalyzing the esterification of diacylglycerol with a fatty acyl CoA substrates, the subject proteins are incapable of esterifying, at least to any substantial extent, the following substrates: cholesterol, 25-hydroxy-, 27-hydroxy-,7α-hydroxy- or 7β-hydroxycholesterols, 7-ketocholesterol, vitamins D2 and D3, vitamin E, dehydrepiandrosterone, retinol, ethanol, sitosterol, lanosterol and ergosterol.

The term polyeptide composition as used herein refers to both the full length proteins as well as portions or fragments thereof. Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses a DGAT enzyme, be that species animal or plant. In the following description of the subject invention, the term DGAT is used to refer not only to the human form of the enzyme, but also to homologs thereof expressed in non-human species, including plant species.

The subject DGAT proteins are, in their natural environment, trans-membrane proteins. The subject proteins are characterized by the presence of at least one potential N-linked glycosylation site, at least one potential tyrosine phosphorylation site, and multiple hydrophobic domains, including 6 to 12 hydrophobic domains capable of serving as transmembrane regions. The proteins range in length from about 400 to 650, usually from about 475 to 525 and more usually from about 485 to 500 amino acid residues, and the projected molecular weight of the subject proteins based solely on the number of amino acid residues in the protein ranges from about 50 to 80, usually from about 55 to 75 and more usually from about 60 to 65 kDa, where the actual molecular weight may vary depending on the amount of glycolsylation of the protein and the apparent molecular weight may be considerably less (e.g. 40 to 50 kDa) because of SDS binding on gels.

The amino acid sequences of the subject proteins are characterized by having at least some homology to a corresponding ACAT protein from the same species, e.g. a human DGAT protein has at least some sequence homology with the human ACAT-1 protein, the mouse DGAT protein has at least some sequence homology with the mouse ACAT-1 protein, etc., where the sequence homology will not exceed about 50%, and usually will not exceed about 40% and more usually will not exceed about 25%, but will be at least about 15% and more usually at least about 20%, as determined using GCG (Genetics Computer Group, Wisconsin Package, Standard Settings, Gap Creation Penalty 3.0, Gap Extension Penalty 0.1).

Of particular interest in many embodiments are proteins that are non-naturally glycosylated. By non-naturally glycosylated is meant that the protein has a glycosylation pattern, if present, which is not the same as the glycosylation pattern found in the corresponding naturally occurring protein. For example, human DGAT of the subject invention and of this particular embodiment is characterized by having a glycosylation pattern, if it is glycosylated at all, that differs from that of naturally occurring human DGAT. Thus, the non-naturally glycosylated DGAT proteins of this embodiment include non-glycosylated DGAT proteins, i.e. proteins having no covalently bound glycosyl groups.

Of particular interest in certain embodiments is the human DGAT protein, where the human DGAT protein of the subject invention has an amino acid sequence that comprises a region substantially the same as or identical to the sequence appearing as SEQ ID NO:04 infra. By substantially the same as is meant a protein having a region with a sequence that has at least about 75%, usually at least about 90% and more usually at least about 98% sequence identity with the sequence of SED ID NO:04, as measured by GCG or BLAST, supra. Of particular interest in other embodiments is the mouse DGAT protein, where the mouse DGAT protein of the subject invention has an amino acid sequence that is substantially the same as or identical to the sequence appearing as SEQ ID NO:05, infra. Also of particular interest in yet other embodiments of the subject invention is the A. thaliana DGAT protein, where the A. thaliana DGAT protein of the subject invention has an amino acid sequence encoded by the nucleic acid having the sequence appearing as SEQ ID NO:03, infra.

In addition to the specific DGAT proteins described above, homologs or proteins (or fragments thereof) from other species, i.e. other animal or plant species, are also provided, where such homologs or proteins may be from a variety of different types of species, including animals, such as mammals, e.g. rodents, such as mice, rats; domestic animals, e.g. horse, cow, dog, cat; and humans, as well as non-mammalian species, e.g. avian, insect and the like, as well plant species. By homolog is meant a protein having at least about 35%, usually at least about 40% and more usually at least about 60% amino acid sequence identity the specific DGAT proteins as identified in SEQ ID NOS: 04 to 06, where sequence identity is determined using GCG or BLAST, supra.

The DGAT proteins of the subject invention (e.g. human DGAT or a homolog thereof) are present in a non-naturally occurring environment, e.g. are separated from their naturally occurring environment. In certain embodiments, the subject DGAT is present in a composition that is enriched for DGAT as compared to DGAT in its naturally occurring environment. As such, purified DGAT is provided, where by purified is meant that DGAT is present in a composition that is substantially free of non DGAT proteins, where by substantially free is meant that less than 90%, usually less than 60% and more usually less than 50% of the composition is made up of non-DGAT proteins. For compositions that are enriched for DGAT proteins, such compositions will exhibit a DGAT activity of at least about 100, usually at least about 200 and more usually at least about 1000 pmol triglycerides formed/mg protein/min, where such activity is determined by the assay described in the Experimental Section, infra.

In certain embodiments of interest, the DGAT protein is present in a composition that is substantially free of the constituents that are present in its naturally occurring environment. For example, a human DGAT protein comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's constituents will still be present in the composition prepared from the naturally occurring source.

The DGAT of the subject invention may also be present as an isolate, by which is meant that the DGAT is substantially free of both non-DGAT proteins and other naturally occurring biologic molecules, such as oligosaccharides, polynucleotides and fragments thereof, and the like, where substantially free in this instance means that less than 70%. usually less than 60% and more usually less than 50% of the composition containing the isolated DGAT is a non-DGAT naturally occurring biological molecule. In certain embodiments, the DGAT is present in substantially pure form, where by substantially pure form is meant at least 95%, usually at least 97% and more usually at least 99% pure.

In addition to the naturally occurring DGAT proteins, DGAT polypeptides which vary from the naturally occurring DGAT proteins are also provided. By DGAT polypeptides is meant proteins having an amino acid sequence encoded by an open reading frame (ORF) of a DGAT gene, described supra, including the full length DGAT protein and fragments thereof, particularly biologically active fragments and/or fragments corresponding to functional domains; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to a DGAT protein of SEQ ID NO:4, SEQ ID NO:05, SEQ ID NO:06 or a homolog thereof; of at least about 10 aa, and usually at least about 15 aa, and in many embodiments at least about 50 aa in length.

PREPARATION OF DGAT POLYPEPTIDES

The subject DGAT proteins and polypeptides may be obtained from naturally occurring sources, but are preferably synthetically produced. Where obtained from naturally occurring sources, the source chosen will generally depend on the species from which the DGAT is to be derived.

The subject DGAT polypeptide compositions may be synthetically derived by expressing a recombinant gene encoding DGAT, such as the polynucleotide compositions described above, in a suitable host. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a DGAT gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. -galactosidae, etc.

Expression cassettes may be prepared comprising a transcription initiation region, the gene or fragment thereof, and a transcriptional termination region. Of particular interest is the use of sequences that allow for the expression of fictional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

DGAT proteins and polypeptides may be expressed in prokaryotes or eukaryotes in accordance with conventional ways, depending upon the purpose for expression. For large scale production of the protein, a unicellular organism, such as *E. coli B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the DGAT gene in eukaryotic cells, where the DGAT protein will benefit from native folding and post-translational modifications. Small peptides can also be synthesized in the laboratory. Polypeptides that are subsets of the complete DGAT sequence may be used to identify and investigate parts of the protein important for fumction.

Once the source of the protein is identified and/or prepared, e.g. a transfected host expressing the protein is prepared, the protein is then purified to produce the desired DGAT comprising composition. Any convenient protein purification procedures may be employed, where suitable protein purification methodologies are described in Guide to Protein Purification, (Deuthser ed.) (Academic Press, 1990). For example, a lysate may prepared from the original source, e.g. naturally occurring cells or tissues that express DGAT or the expression host expressing DGAT, and purified using HPLC, exclusion chromatography, gel electrophoresis, affinity chromatography, and the like.

METHODS AND COMPOSITIONS HAVING RESEARCH APPLICATION

Also provided by the subject invention are methods and compositions having research applications, such as in the study of the acylglycerol metabolism, in the identification of key components of the triglyceride synthesis pathway, in the identification of triglyceride synthesis modulatory agents, e.g. DGAT inhibitors or enhancers, and the like.

The subject nucleic acid compositions find use in a variety of research applications. Research applications of interest include: the identification of DGAT homologs; as a source of novel promoter elements; the identification of DGAT expression regulatory factors; as probes and primers in hybridization applications, e.g. PCR; the identification of expression patterns in biological specimens; the preparation of cell or animal models for DGAT function; the preparation of in vitro models for DGAT function; etc.

Homologs of DGATare identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when ubjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided DGAT sequences, e.g. allelic variants, genetically altered versions of the gene, etc., bind to the provided DGAT sequences under stringent hybridization conditions. By using probes, particularly labeled probes of DNA sequences, one can isolate homologous or related genes. One can also use sequence information derived from the polynucleotide compositions of the subject invention to prepare electronic "probes" for use in searching of computer based sequence date, e.g. BLAST searches EST databases.

The sequence of the 5' flanking region of the subject nucleic acid compositions may be utilized as a source for promoter elements, including enhancer binding sites, that provide for developmental regulation in tissues where DGAT is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of DGAT expression, especially in different tissues or stages of development, and to identify cis acting sequences and trans-acting factors that regulate or mediate DGATexpression. Such transcription or translational control regions may be operably linked to a DGAT gene in order to promote expression of wild type or altered DGAT or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or MRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the MnRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of DGAT gene expression in the sample.

The sequence of a DGAT gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system. HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of DGAT, or to alter properties of the protein that affect its function or regulation.

The subject nucleic acids can be used to generate transgenic hosts, e.g non-human animals, such as mice, cows, rats, pigs etc., plants, fungi, or site specific gene modifications in cell lines. Using the nucleic acid compositions of the subject invention, standard protocols known to those of skill in the art may used to produce such transgenic hosts that have been genetically manipulated with respect to the DGAT gene, i.e. DGAT transgenic hosts.

Transgenic animals may be made through homologous recombination, where the normal DGAT locus is altered. Alternatively, a nucleic acid construct is randomly integrated into the genome. Vectors for stable integration include plasmids, retroviruses and other animal viruses, YACs, and the like. DNA constructs for homologous recombination will comprise at least a portion of the DGAT gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g mouse, rat, guinea pig, cow, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The resultant chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc.

Transgenic plants may produced in a similar manner. Methods of preparing transgenic plant cells and plants are described in U.S. Pat. Nos. 5,767,367; 5,750,870; 5,739, 409; 5,689,049; 5,689,045; 5,674,731; 5,656,466; 5,633, 155; 5,629,470; 5,595,896; 5,576,198; 5,538,879; 5,484, 956; the disclosures of which are herein incorporated by reference. Methods of producing transgenic plants are also reviewed in Plant Biochemistry and Molecular Biology (eds Lea & Leegood, John Wiley & Sons)(1993) pp 275–295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is Agrobacterium mediated transformation. With Agrobacterium mediated transformation, co-integrative or binary vectors comprising the exogenous DNA are prepared and then introduced into an appropriate Agrobacterium strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

The modified cells, animals or plants are useful in the study of DGAT function and regulation. For example, a series of small deletions and/or substitutions may be made in the host's native DGAT gene to determine the role of different exons in pathogenesis, signal transduction, etc. Specific constructs of interest include anti-sense DGAT, which will block DGAT expression, expression of dominant negative DGAT mutations, and over-expression of DGAT genes. Where a DGAT sequence is introduced, the introduced sequence may be either a complete or partial sequence of a DGAT gene native to the host, or may be a complete or partial DGAT sequence that is exogenous to the host animal, e.g., a human DGAT sequence. A detectable marker, such as lac Z may be introduced into the DGAT locus, where upregulation of DGAT expression will result in an easily detected change in phenotype. One may also provide for expression of the DGAT gene or variants thereof in cells or tissues where it is not normally expressed, at levels not normally present in such cells or tissues, or at abnormal times of development. The transgenic hosts, e.g. animals, plants, etc., may be used in functional studies, drug screening, etc., e.g. to determine the effect of a candidate drug on DGAT activity.

The subject polypeptide compositions can be used to produce in vitro models of triglyceride synthesis, where such models will consist of the subject DGAT proteins and other components of triglyceride synthesis, e.g. substrates, such as diacylglycerol or metabolic precersors thereof, fatty acyl CoAs and the like, other components of the triacylglycerol synthetase complex, e.g. acyl CoA ligase, acyl CoA acyltransferase, monoacyl glycerol acyltransferase, etc.

Also provided by the subject invention are screening assays designed to find modulatory agents of DGAT activity, e.g. inhibitors or enhancers of DGAT activity, as well as the agents identified thereby, where such agents may find use in a variety of applications, including as therapeutic agents, as agricultural chemicals, etc. The screening methods will typically be assays which provide for qualitative/quantitative measurements of DGAT activity in the presence of a particular candidate therapeutic agent. For example, the assay could be an assay which measures the acylation activity of DGAT in the presence and absence of a candidate inhibitor agent. The screening method may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Using the above screening methods, a variety of different therapeutic agents may be identified. Such agents may target the enzyme itself, or an expression regulator factor thereof. Such agents may inhibitors or promoters of DGAT activity, where inhibitors are those agents that result in at least a reduction of DGAT activity as compared to a control and enhancers result in at least an increase in DGAT activity as compared to a control. Such agents may be find use in a variety of therapeutic applications, as described in greater detail below.

METHODS AND COMPOSITIONS HAVING MEDICAL APPLICATIONS

The methods and compositions of the subject invention also have broad ranging applications in a variety of medical applications, including diagnostic screening, therapeutic treatments of pathological conditions, in the regulation of DGAT activity in desirable ways, and the like.

The subject invention provides methods of screening individuals for a predisposition to a disease state or the presence of disease state, where such screening may focus on the presence of one or more markers, such as a mutated DGAT gene or expression regulatory element thereof, observed levels of DGAT; the expression level of the DGAT gene in a biological sample of interest; and the like.

Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal DGAT in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of DGAT. Biochemical studies may be performed to determine whether a sequence polymorphism in a DGAT coding region or control regions is associated with disease. Disease associated polymorphisms may include deletion or truncation of the gene, mutations that alter expression level, that affect the activity of the protein, etc.

Changes in the promoter or enhancer sequence that may affect expression levels of DGAT can be compared to expression levels of the normal allele by various methods known in the art. Methods for determining promoter or enhancer strength include quantitation of the expressed natural protein; insertion of the variant control element into a vector with a reporter gene such as P-galactosidase, luciferase, chloramphenicol acetyltransferase, etc. that provides for convenient quantitation; and the like.

A number of methods are available for analyzing nucleic acids for the presence of a specific sequence, e.g a disease associated polymorphism. Where large amounts of DNA are available, genomic DNA is used directly. Alternatively, the region of interest is cloned into a suitable vector and grown in sufficient quantity for analysis. Cells that express DGAT may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g $^{32}p$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type DGAT sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in DGAT may be based on the functional or antigenic characteristics of the protein. Protein truncation assays are useful in detecting deletions that may affect the biological activity of the protein. Various immunoassays designed to detect polymorphisms in DGAT proteins may be used in screening. Where many diverse genetic mutations lead to a particular disease phenotype, functional protein assays have proven to be effective screening tools. The activity of the encoded DGAT protein may be determined by comparison with the wild-type protein.

Diagnostic methods of the subject invention in which the level of DGAT expression is of interest will typically involve comparison of the DGAT nucleic acid abundance of a sample of interest with that of a control value to determine any relative differences, where the difference may be measured qualitatively and/or quantitatively, which differences are then related to the presence or absence of an abnormal DGAT expression pattern. A variety of different methods for determining the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, *Mol. Biotechnol*. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

The subject diagnostic or screening methods may be used to identify the presence of, or predisposition to, disease conditions associated with acylglycerol metabolism, particular those associated with DGAT activity. Such disease conditions include: hyperlipidemia, cardiovascular disease, obesity, diabetes, cancer, neurological disorders, immunological disorders, and the like.

Also provided are methods of regulating, including enhancing and inhibiting, DGAT activity in a host. A variety of situations arise where modulation of DGAT activity in a host is desired, where such conditions include disease conditions associated with DGAT activity and non-disease condition in which a modulation of DGAT activity is desired for a variety of different reasons.

For the modulation of DGAT activity in a host, an effective amount of active agent that modulates the activity, e.g. reduces the activity, of DGAT in vivo, is administered to the host. The active agent may be a variety of different compounds, including: the polynucleotide compositions of the subject invention, the polypeptide compositions of the subject invention, a naturally occurring or synthetic small molecule compound, an antibody, fragment or derivative thereof, an antisense composition, and the like.

The nucleic acid compositions of the subject invention find use as therapeutic agents in situations where one wishes to enhance DGAT activity in a host, e.g. in a mammalian host in which DGAT activty is low resulting in a disease condition, etc. The DGAT genes, gene fragments, or the encoded DGAT protein or protein fragments are useful in gene therapy to treat disorders associated with DGAT defects. Expression vectors may be used to introduce the DGATgene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Of particular interest are those agents identified by the screening assays of the subject invention, as described above.

Also of interest as active agents are antibodies that modulate, e.g. reduce, if not inhibit, DGAT activity in the host. Suitable antibodies are obtained by immunizing a host animal with peptides comprising all or a portion of a DGAT protein, such as the DGAT polypeptide compositions of the subject invention. Suitable host animals include mouse, rat sheep, goat, hamster, rabbit, etc. The origin of the protein immunogen may be mouse, human, rat, monkey etc. The host animal will generally be a different species than the immunogen, e.g. human DGAT used to immunize mice, etc.

The immunogen may comprise the complete protein, or fragments and derivatives thereof. Preferred immunogens comprise all or a part of DGAT, where these residues contain the post-translation modifications, such as glycosylation. found on the native DGAT. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with DGAT, where the DGAT will preferably be in substantially pure form, comprising less than about 1% contaminant. The immunogen may comprise complete DGAT, fragments or derivatives thereof. To increase the immune response of the host animal, the DGAT may be combined with an adjuvant, where suitable adjuvants include alum, dextran, sulfate, large polymeric anions, oil & water emulsions, e.g. Freund's adjuvant, Freund's complete adjuvant, and the like. The DGAT may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The DGAT is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using DGAT bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu etal. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector fuctions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g SV-40early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of DGAT in the host. Antisense molecules can be used to down-regulate expression of DGAT in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'- deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigeltman et al. (1995), *Nucl. Acids Res.* 23:4434–42). Examples of oligonucleotides with catalytic activity are escribed in WO 9506764. Conjugates of anti-sense ODN with a metal complex, e.g. erpyridylCu(II), capable of mediating mRNA hydrolysis are described in Bashkin et al. (1995), *Appl. Biochem. Biotechnol.* 54:43–56.

As mentioned above, an effective amount of the active agent is administered to the most, where "effective amount" means a dosage sufficient to produce a desired result, where the desired result in the desired modulation, e.g. enhancement, reduction, of DGAT activity.

In the subject methods, the active agent(s) may be administered to the host using any convenient means capable of resulting in the desired effect. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulations to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DGAT DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving acylglycerol metabolism, and particularly DGAT activity, including both insufficient or hypo-DGAT activity and hyper-DGAT activity. Representative diseases that may be treated according to the subject methods include: hyperlipidemia, cardiovascular disease, obesity, diabetes, cancer, neurological disorders, immunological disorders, skin disorders associated with sebaceous gland activity, e.g. acne, and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as serum triglyceride level, weight, etc. As such, treatment also includes situations where the pathological condition, or at least symptoms associated therewith, are completely inhibited, e.g prevented from happening, or stopped, e.g. terminated, such that the host no longer suffers from the pathological condition, or at least the symptoms that characterize the pathological condition. For example, where the disease condition is marked by the presence of elevated lipid levels, treatment includes at least a reduction in the observed lipid levels, including a restoration of normal lipid levels. As another example, where the disease is obesity, treatment results in at least a reduction in the overall weight of the host.

The subject methods also find use in the modulation of DGAT activity in hosts not suffering from a disease condition but in which the modulation of DGAT activity is nonetheless desired. For example, sperm production in males has been associated with DGAT activity. As such, in males where at least reduced sperm production is desired, the subject methods can be used to reduce DGAT activity in such males, e.g. by administering an agent that reduces DGAT activity in such males, where such agents are described above. In other words, the subject methods provide a means of male contraception. Alternatively, where increased sperm count in a given male is desired, e.g. in those conditions where the male has reduced fertility, the subject methods can be used to enhance DGAT activity in the male and thereby increase sperm count and fertility, e.g. by administering to the male host a DGAT enhancing agent, as described above.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

METHODS AND COMPOSITIONS FOR PRODUCING TRIGLYCERIDES AND TRIGLYCERIDE COMPOSITIONS

Also provided by the subject invention are methods for preparing triglycerides and triglyceride comprising compositions, as well as the compositions produced by these methods. In preparing triglycerides with the subject invention, at least the direct substrates of the desired triacylglyercol, e.g. diacylglycerol and fatty acyl CoA, will be combined in the presence of the polypeptide under conditions sufficient for the acylation of the diacylglycerol to occur. The synthesis may occur in an in vitro system, e.g. in a vessel in which the substrates or precursors thereof and the DGAT enzyme, as well as any other requisite enzymes (e.g. as need to convert the substrate precursors to substrates), or an in vivo system, e.g. a host cell that naturally comprises the substrates and into which a DGAT gene has been inserted in a manner sufficient for expression of the DGAT gene, where the resultant triglyceride products may be separated from the host cell using standard separation techniques.

Of interest for use in producing triglyceride compositions are transgenic plants/fungi that have been genetically manipulated using the nucleic acid compositions of the subject invention to produce triglycerides and/or compositions thereof in one or more desirable ways. Transgenic plants/fungi of the subject invention are those plants/fungi that at least: (a) produce more triglyceride or triglyceride composition than wild type, e.g. produce more oil, such as by producing seeds having a higher oil content, as compared to wild-type; (b) produce triglyceride compositions, e.g. oils, that are enriched for triglycerides and/or enriched for one or more particular triglycerides as compared to wild type; and the like. Of interest are transgenic plants that produce commercially valuable triglyceride compositions or oils, such as canola, rapeseed, palm, corn, etc., containing various poly- and mono-unsaturated fatty acids, and the like. Of particular interest are transgenic plants, such as canola, rapeseed, palm, oil, etc., which have been genetically modified to produce seeds having higher oil content than the content found in the corresponding wild type, where the oil content of the seeds produced by such plants is at least 10% higher, usually at least 20% higher, and in many embodiments at least 30% higher than that found in the wild type, where in many embodiments seeds having oil contents that are 50% higher, or even greater, as compared to seeds produced by the corresponding wild-type plant, are produced. The seeds produced by such DGAT transgenic plants can be used as sources of oil or as sources of additional DGAT transgenic plants. Such transgenic plants and seeds therefore find use in methods of producing oils. In such methods, DGAT transgenic plants engineered to produce seeds having a higher oil content than the corresponding wild-type, e.g. seeds in which the DGAT gene is overexpressed, are grown, the seeds are harvested and then processed to recover the oil. The subject transgenic plants can also be used to produce novel oils characterized by the presence of triglycerides in different amounts and/or ratios than those observed in naturally occurring oils. The transgenic plants/fungi described above can be readily produced by those of skill in the art armed with the nucleic acid compositions of the subject invention. See the discussion on how to prepare transgenic plants, supra.

The triglyceride compositions described above find use in a variety of different applications. For example, such compositions or oils find use as food stuffs, being used as ingredients, spreads, cooking materials, etc. Alternatively, such oils find use as industrial feedstocks for use in the production of chemicals, lubricants, surfactants and the like.

Also of interest are transgenic non-human animals suitable for use as sources of food products and/or animal based industrial products. Such trans-genic non-human animals, e.g. transgenic mice, rats, livestock, such as cows, pigs, horses, birds, etc, may be produced using methods known in the art and reviewed supra. Such trans-genic non-human animals can be used for sources of a variety of different food and industrial products in which the triglyceride content is specifically tailored in a desirable manner. For example, such trans-genic animals that have been modified in a manner such that DGAT activity is reduced as compared to the wild type can be used as sources of food products that are low in triglyceride content, e.g. low fat or lean meat products, low fat milk, low fat eggs, and the like.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

I. Cloning of DGAT cDNA.

ESTs (accession numbers R07932 (human) and W10786 (mouse)) with sequence similarity to ACAT were identified from BLAST searches of the databases. The 5' end of the DGAT cDNA was obtained by using 5' RACE and a mouse spleen Marathon Ready™ cDNA library (Clontech, Palo Alto, Calif.). The sequences were deposited in GenBank (accession numbers XXXXXX).

The translation of a full-length cDNA for the mouse EST (SEQ ID NO.2) predicts an open reading frame encoding a 498-amino acid protein that is ~20% identical to mouse ACAT, with the most highly conserved regions in the C-terminus. The predicted protein sequence (SEQ ID NO.5) contains a potential N-linked glycosylation site and a putative tyrosine phosphorylation site. A serine residue found in ACAT that is necessary for enzyme activity (as reported in Cao et al., J. Biol. Chem. (1996) 271:14642–14648) appears to be conserved. The protein has multiple hydrophobic domains and 6–12 possible transmembrane domains. Analysis by a transmembrane region prediction program (http://ulrec3.unil.ch/software/TMPRED_form.html) favors nine transmembrane domains (amino acids 96–114, 140–157, 174–198, 200–218, 293–311, 337–360, 412–434, 436–456, and 461–484).

Insect cell expression studies. DGAT coding sequences with or without an N-terminal FLAG epitope (IBI, Kodak, New Haven, Conn.) (MG<u>DYKDDDDG</u>-, epitope underlined (SEQ ID NO:06)) were subcloned into the baculovirus transfer vector pVL 1392 (PharMingen, San Diego, Calif.). High titers of recombinant baculoviruses were obtained by cotransfection of ACAT or DGAT baculovirus transfer vectors with viral BaculoGold™ DNA (PharMingen), followed by plaque purification and virus amplification in Sf9 cells (cultured in Grace's medium (Life Technologies, Grand Island, N.Y.) and 10% fetal bovine serum). H5 insect cells (cultured in serum-free Express-Five medium (Life Technologies)) were plated on day 0 ($8.5 \times 10^6$ cells/100-mm dish) and infected on day 1 with high titers of virus at a multiplicity of infection (MOI) that was empirically determined. On day 3, cells were collected by centrifugation and washed wice with phosphate-buffered saline (PBS). Cell pellets were homogenized by 10 passages through a 27-G needle in 0.1 M sucrose, 50 mM Kcl, 40 mM $KH_2PO_4$, 30 mM DTA (pH 7.2). Total membrane fractions (100,000×g pellet) were resuspended in the homogenization buffer and frozen (–80° C.). Immunoblots of membrane proteins (75 µg) were performed using the anti-FLAG M2 monoclonal antibody (IBI, Kodak).

For metabolic labeling experiments, H5 insect cells were plated on day 0 at $2.9 \times 10^6$ cells per 60-mm dish and infected on day 1 with high titers of viruses. On day 3, cells were washed and incubated in methionine- and cysteine-free medium (SF900 II, Life Technologies) for 2 h, followed by incubation in the same medium containing 715 µCi of [$^{35}$S]methionine and [$^{35}$S]cysteine (Amersham Pro-Mix) for 1 h. Cells were washed twice with PBS, collected by low-speed centrifugation, and the cell pellet was resuspended in 0.5 ml of 50 mM Tris-HCl, 150 mM NaCl, 5 mM EDTA, 1 mM PMSF, 1% Triton X-100 (pH 7.4) and sonicated. Cellular protein samples (100 mg) were analyzed by SDS-PAGE and autoradiography.

For ACAT assays, cell-membrane proteins (100 µg) were assayed by using [1-$^{14}$C]oleoyl CoA (51 mCi/mmol, Amersham, Arlington Heights, Ill.) and cholesterol/egg phosphatidyl choline (PC) liposomes (molar ratio=0.7) as described in Smith et al., J. Lipids Res. (1995) 36:641–652. In some assays, other acyl acceptors were substituted for cholesterol in the liposomes at a 0.2 molar ratio (acceptor:egg PC) to test their ability to act as substrates. Incorporation of the [$^{14}$C]oleoyl group into products was assessed by thin-layer chromatography, followed by autoradiography. DGAT assays were based on assays optimized for rat liver. See Andersson supra, Ozasa et al., J. Lipids Res. (1989) 30:1759–1762; and S. K. Erickson, K. Pella, S. Lear, manuscript in preparation. The incorporation of [$^{14}$C]oleoyl CoA into triacylglycerol was measured under apparent $V_{MAX}$ conditions by using exogenous diacylglycerol provided as diacylglycerol:egg PC liposomes (molar ratio ~0.16). Cell-membrane proteins (20–25 µg) were assayed in 0.25 M sucrose, 1 mM EDTA, 150 mM $MgCl_2$, 100 mM Tris-HCl (pH 7.5) containing 250 µg of bovine serum albumin and 20 µg of diacylglycerol in liposomes (final volume=0.2 ml) and 5 nmol [$^{14}$C]oleoyl CoA (40,000 dpm/nmol). Reactions were carried out for 5 min, and the products analyzed as described in Erickson et al., J. Lipids Res. (1980) 21: 930–941. Similar assays were performed with 1-stearoyl-2-[1-$^{14}$C]arachidonyl-sn-glycerol (53 mCi/mmol, Amersham) diluted to a final activity of 38,000 dpm/nmol with unlabeled 1,2-diacyl-sn-glycerol and unlabeled oleoyl CoA.

Relative triacylglycerol and DAG masses were determined by total lipid extraction of membranes or cells followed by thin-layer chromatography, iodine vapor visualization, photography of the plates, and densitometric analysis. Triolein standards were used to estimate mass of triacylglycerols, and DAG units were estimated relative to one another. Triacylglycerol values were normalized to I for wild-type virus-infected cell membranes to correct for inter-experiment variability.

Cells infected with the virus containing DGAT cDNA expressed a ~47-kDa protein at high levels in the membrane fraction, but lacked detectable cholesterol esterification activity as compared with ACAT virus-infected cells. Using a variety of other possible acyl acceptors as provided substrates (including 25-hydroxy-, 27-hydroxy-, 7α-hydroxy- or 7β-hydroxycholesterols, 7-ketocholesterol, vitamins D2 and D3, vitamin E, dehydroepiandrosterone, retinol, ethanol, sitosterol, lanosterol, and ergosterol), no acyltransferase activity was detected in H5 membranes expressing the protein, as assessed by autoradiography of thin-layer chromatography plates used to analyze reaction products. However, further analysis of these plates revealed that membranes from these cells had significantly increased triacylglycerol mass (as assessed by $I_2$ visualization) and incorporated significantly more [$^{14}$C]oleoyl CoA into triacylglycerols than did membranes from wild-type virus-infected cells (197 vs. 55 pmol/mg prot/min). These data suggested that the identified cDNA might encode a DGAT.

Measurements of DGAT activity in membranes from H5 insect cells expressing the putative DGAT cDNA revealed that DGAT activity in these membranes was more than fivefold higher than that in membranes from wild-type virus-infected cells. The DGAT activity level increased proportionately with the amount of FLAG-tagged protein expressed in membranes isolated from cells harvested at different time points following infection. DGAT activity levels were similar regardless of whether [$^{14}$C] diacylglycerol or [$^{14}$C]oleoyl CoA was used as the labeled substrate. In the absence of added oleoyl CoA, [$^{14}$C] diacylglycerol was not incorporated into triacylglycerols. Additionally, [$^{3}$H]oleic acid was not incorporated into triacylglycerols in DGAT virus-infected membranes (7±6 vs. 49±47 pmol triacylglycerol/mg prot/min for wild-type, n=3), establishing the requirement for a fatty acyl CoA. Triacylglycerol mass was more than 10-fold higher in membranes from DGAT virus-infected cells than in membranes from wild-type virus-infected cells (11±7 vs. 1±0.5 pg/µg membrane protein, P=0.04, n=5). No change in relative DAG mass was observed (0.33±0.05 vs. 0.34±0.12 units for DGAT and wild-type, respectively).

mRNA expression. Human Multiple Tissue northern blots (Clontech) were hybridized with a $^{32}$P-labeled 1.1-kb human DGAT fragment from the human EST. For mouse tissues, total RNA was prepared with Trizol reagent (Life Technologies), and samples (10 mg) were analyzed by northern blotting using a $^{32}$P-labeled, 1-kb mouse DGAT fragment from the mouse EST. Blots were stripped and sequentially reprobed for G3PDH and 28S RNA as described in Barbu & Dautry, Nucleic Acids Res. (1989) 17:7115. Bands in autoradiograms from the 3T3-L1 experiments were quantified with a phosphoimager (Fuji Medical Systems, Stamford, Conn.).

mRNA expression was detected in every human and mouse tissue examined, as expected for DGAT's role in cellular glycerolipid metabolism. The highest expression levels were found in the small intestine, consistent with a proposed role for DGAT in intestinal fat absorption (see Brindley supra, and Mansbach, Biochim. Biophys. Acta (1973) 296:386–402. Additionally, mRNA was expressed in mouse adipose tissue, a tissue known to have high DGAT activity (see Coleman & Bell, supra). Interestingly, mRNA expression was not particularly high in the livers of humans or mice, despite the fact that liver tissue possesses DGAT activity (as reported in Polokoff & Bell, Biochim. Biophys. Acta (1980)35:535–545.

NIH 3T3-L1 differentiation. NIH 3T3-L1 fibroblasts were cultured in Dulbecco's Modified Eagle's medium supplemented with 10% fetal bovine serum, 100 units/ml penicillin, 100 µg/ml streptomycin, and 2 mM L-glutamine. The differentiation of 3T3-L1 cells into adipocytes was induced by incubating confluent monolayers of cells in serum-containing medium supplemented with $10^{-5}$ M dexamethasone, 0.5 mM isobutylmethylxanthine and 10 µg/ml insulin as described Brasaemle et al., J. Lipid Res. (1997) 38:2249–2263.

It was found that mRNA expression increased markedly in parallel with DGAT activity in NIH 3T3-L1 cells during their differentiation into adipocytes, a process known to be associated with increases in DGAT activity (see Coleman et al., J. Biol. Chem. (1978) 253:7256–7261) and triacylglycerol mass accumulation (see Green & Kehinde, Cell (1975) 5:19–27.

The above results indicate that the cDNA encodes a DGAT protein. As a final piece of evidence confirming the identity of this cDNA, the mouse DGAT gene in embryonic stem cells was disrupted and germline transmission of this mutation was acheived. In preliminary experiments, the DGAT activity in membranes from embryonic fibroblasts homozygous for the knockout mutation (−/−) are markedly reduced compared with that in wild-type fibroblasts (25.5±2.6 vs. 453.6±4.5 pmol triacylglycerol/mg prot/min for −/− and +/+, respectively; P<0.001). Taken together, the experimental data indicate that the identified cDNA encodes a DGAT catalytic unit.

Gene mapping. Primers derived from the human EST sequences were used to identify genomic clones in an arrayed BAC library according to manufacturer's protocol (Research Genetics, Huntsville, Ala.). The BAC clone was mapped to chromosome 8qter by fluorescent in situ hybridization as described in Stokke et al., Genomics (1995) 26:134–137. The clone (RMC08P049) may be requested from the website (http://rmc-www.lbl.gov). Linkage analysis for mouse gene mapping was performed with a panel of 67 progeny derived from a ((C57BL/6J×Mus spretus) F1×C57BL/6J) interspecific backcross as described in Warden et al., Genomics (1993) 18:295–307. This backcross panel has been typed for more than 400 loci distributed throughout the genome. See Welch et al., J. Lipid Res. (1996) 37:1406–1421. Briefly, parental strain DNAs were screened for restriction fragment-length variants by restriction enzyme digestion and hybridization with a radiolabeled, 1-kb mouse DGAT cDNA fragment as described in Warden, supra. Filters were washed in 1.0×SSC/0.1% SDS, at 50° C., for 20 min. Autoradiograms were exposed for 3 days at −70° C. Linkage to previously typed chromosomal markers was detected by using Map Manager v.2.6.5, and loci were ordered by minimizing the number of recombination events between DGAT and the markers. See Manly, Mamm. Genome (1993)4:303–313. The mouse homolog for the DGAT gene (DGAT) was mapped to a region of chromosome 15 that exhibits homology with human chromosome 8. The mouse DGAT gene was found to be colocalized with quantitative trait loci for plasma levels of triacylglycerol-rich lipoproteins.

Identification of DGAT cDNA from Arabidopsis thaliana. The plant (A.thaliana) DGAT gene (#AA042298) (SEQ ID NO:03) was identified from BLAST searches of the EST database using mouse DGAT sequences as a probe. The plant DGAT EST protein sequences encoded by plant DGAT genes are 40–50% identical to mammalian DGAT enzymes. Furthermore, the plant DGAT sequences are more closely related to other mammalian DGAT sequences than to ACAT protein sequences.

It is apparent from the above results and discussion that polynucleotides encoding both animal and plant DGAT enzymes, as well as novel polypeptides encoded thereby, are provided. The subject invention is important for both research and therapeutic applications. Using the DGAT probes of the subject invention, the role of DGAT and its regulation in a number of physiological processes can be studied in vivo. The subject invention also provides for important new ways of treating diseases associated with DGAT, such as hypertriglycemia and obesity, as well as in the production of tryglycerides.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated polynucleotide that comprises SEQ ID NO:02.

2. An expression cassette comprising a transcriptional initiation region functional in an expression host, a polynucleotide according to claim 1 under the transcriptional regulation of said transcriptional initiation region, and a transcriptional termination region functional in said expression host.

3. A cell comprising an expression cassette according to claim 2 as part of an extrachromosomal element or integrated into the genome of a host cell as a result of introduction of said expression cassette into said host cell, or the cellular progeny thereof.

4. A method of producing a polypeptide having DGAT activity, said method comprising:
   growing a cell according to claim 3, whereby said polypeptide is expressed; and
   isolating said polypeptide substantially free of other proteins.

* * * * *

UNITED STATES PATENT AND TRADEMARK OFFICE
CERTIFICATE OF CORRECTION

PATENT NO. : 6,344,548 B1  
DATED : February 5, 2002  
INVENTOR(S) : Farese, Jr. et al.

Page 1 of 1

It is certified that error appears in the above-identified patent and that said Letters Patent is hereby corrected as shown below:

<u>Column 36,</u>  
Line 31, under the title "What is claimed is", after the word cellular and before the word thereof, the word progency is misspelled please replace the word with the correct spelling of progeny.

Signed and Sealed this

Thirtieth Day of April, 2002

*Attest:*

*Attesting Officer*

JAMES E. ROGAN  
*Director of the United States Patent and Trademark Office*

UNITED STATES PATENT AND TRADEMARK OFFICE
CERTIFICATE OF CORRECTION

PATENT NO.    : 6,344,548 B1                                                    Page 1 of 1
DATED         : February 5, 2002
INVENTOR(S)   : Farese, Robert V. Jr. et al.

It is certified that error appears in the above-identified patent and that said Letters Patent is hereby corrected as shown below:

Title page,
Item [73], Assignee, it should read
-- The Regents of the University of California, Oakland, California (US)
                And
The Department of Veterans Affairs, Washignton, D.C. (US) --

Column 1,
Delete lines 5-9, and insert the following to read
-- This invention was made with Government support under Grant Nos. R01 52069, and R01 57170, awarded by the National Institutes of Health. The Government has certain rights n this invention. --

Signed and Sealed this

Eighteenth Day of March, 2003

JAMES E. ROGAN
*Director of the United States Patent and Trademark Office*